(12) United States Patent
Wollnik et al.

(10) Patent No.: US 8,138,474 B2
(45) Date of Patent: Mar. 20, 2012

(54) METHOD AND APPARATUS FOR DIGITAL DIFFERENTIAL ION MOBILITY SEPARATION

(75) Inventors: Hermann Wollnik, Fernwald (DE); Gary Eiceman, Las Cruces, NM (US); Dimitrios Papanastasiou, Athens (GR)

(73) Assignee: Shimadzu Corporation, Kyoto-Shi (JP)

( * ) Notice: Subject to any disclaimer, the term of this patent is extended or adjusted under 35 U.S.C. 154(b) by 4 days.

(21) Appl. No.: 12/945,936

(22) Filed: Nov. 15, 2010

(65) Prior Publication Data

US 2011/0057094 A1 Mar. 10, 2011

Related U.S. Application Data

(62) Division of application No. 11/812,886, filed on Jun. 22, 2007, now Pat. No. 7,863,562.

(51) Int. Cl.
*H01J 49/42* (2006.01)
(52) U.S. Cl. ........ 250/292; 250/281; 250/282; 250/290; 250/294; 250/295; 250/287
(58) Field of Classification Search .................. 250/281, 250/282, 290, 292, 294, 295
See application file for complete search history.

(56) References Cited

U.S. PATENT DOCUMENTS

| | | | |
|---|---|---|---|
| 3,621,239 A | 11/1971 | Cohen | |
| 3,639,757 A | 2/1972 | Caroll et al. | |
| 3,697,748 A | 10/1972 | Cohen | |
| 3,812,355 A | 5/1974 | Wernlund et al. | |
| 3,835,318 A | 9/1974 | Fletcher et al. | |
| 5,047,723 A | 9/1991 | Puumalainen | |
| 5,332,938 A | 7/1994 | McEwan | |
| 6,124,592 A * | 9/2000 | Spangler | 250/287 |
| 6,495,823 B1 | 12/2002 | Miller et al. | |
| 6,621,077 B1 | 9/2003 | Guevremont et al. | |
| 6,624,410 B1 | 9/2003 | Voss | |
| 6,774,360 B2 | 8/2004 | Guevremont et al. | |
| 6,965,106 B2 | 11/2005 | Ding et al. | |

(Continued)

FOREIGN PATENT DOCUMENTS

SU 966586 10/1982

(Continued)

OTHER PUBLICATIONS

Papanastasiou et al. "Differential Mobility Separation of Ions Using a Rectangular Asymmetric Waveform" J. Phys. Chem. A, vol. 112, No. 16, Mar. 14, 2008, pp. 3638-3645.

*Primary Examiner* — Jack Berman
*Assistant Examiner* — Michael Logie
(74) *Attorney, Agent, or Firm* — Sughrue Mion, PLLC

(57) ABSTRACT

A method for differential mobility separation of ions using digital-drive based high voltage fast switching electronics. The digital waveform delivered to the spectrometer is characterized by at least two substantially rectangular pulses of different amplitude and polarity. The control circuitry allows for waveform frequency, duty cycle and pulse amplitudes to be varied independently. Balanced as well as unbalanced asymmetric waveforms can be designed for optimum differential mobility separation of ions. The digital drive is designed for differential mobility spectrometers including parallel plate and segmented plate multipoles of planar symmetry, as well as multipoles of cylindrical symmetry, which may optionally be arranged in series. The use of the digital drive establishes alternating electric fields during which the displacement as a result of ion oscillation is determined by mobility coefficients.

1 Claim, 4 Drawing Sheets

U.S. PATENT DOCUMENTS

| | | | |
|---|---|---|---|
| 7,091,481 B2 * | 8/2006 | Miller et al. | 250/288 |
| 7,119,328 B2 * | 10/2006 | Kaufman et al. | 250/281 |
| 7,126,352 B2 | 10/2006 | Beenhard | |
| 7,129,482 B2 * | 10/2006 | Miller et al. | 250/288 |
| 7,170,053 B2 * | 1/2007 | Shvartsburg et al. | 250/287 |
| 2003/0150985 A1 * | 8/2003 | Guevremont et al. | 250/287 |
| 2005/0040330 A1 * | 2/2005 | Kaufman et al. | 250/293 |
| 2005/0109930 A1 | 5/2005 | Hill, Jr. et al. | |
| 2005/0133716 A1 * | 6/2005 | Miller et al. | 250/293 |
| 2005/0156107 A1 * | 7/2005 | Miller et al. | 250/293 |
| 2005/0173629 A1 | 8/2005 | Miller et al. | |
| 2005/0230616 A1 | 10/2005 | Cameron et al. | |
| 2007/0003996 A1 | 1/2007 | Hitt et al. | |
| 2007/0069120 A1 * | 3/2007 | Shvartsburg et al. | 250/287 |
| 2007/0084999 A1 | 4/2007 | Miller et al. | |
| 2007/0181800 A1 | 8/2007 | Jolliffe et al. | |
| 2007/0277589 A1 | 12/2007 | Harden et al. | |
| 2008/0149824 A1 * | 6/2008 | Miller et al. | 250/287 |
| 2008/0210861 A1 * | 9/2008 | Wu et al. | 250/287 |
| 2009/0140138 A1 | 6/2009 | Vandermey | |

FOREIGN PATENT DOCUMENTS

| | | |
|---|---|---|
| WO | 2007/136373 A1 | 11/2007 |

* cited by examiner

METHOD AND APPARATUS FOR DIGITAL DIFFERENTIAL ION MOBILITY SEPARATION

CROSS REFERENCE TO RELATED APPLICATION

This application is a Divisional of application Ser. No. 11/812,886 filed Jun. 22, 2007, the disclosure of which is incorporated herein by reference in its entirety.

BACKGROUND

1. Technical Field

Apparatuses and methods consistent with the present invention relate to a method and apparatus for performing ion separation, and more specifically, use of electronic-drive circuits for a differential mobility spectrometer, and a system and method therefore.

2. Related Art

Gas-phase ion separation techniques become increasingly important either as stand-alone systems or in conjunction with mass spectrometry for the analysis of molecular conformations, through chromatographic or mass separations. One way to analyze mixtures of gas phase ions is to move them through a gas by electric fields. The velocity of motion of these ions is proportional to the electrical fields, and the proportionality factor is "ion mobility", which itself depends on the magnitude of the electric field. If the electric field acts in the direction the ions are moved by the carrier gas, the ions will move through the given length of the electric field a little faster whereby the overall flight times are characteristic of the sizes of the ions and their interactions with the supporting gas atmosphere.

If the electric field acts perpendicularly to the direction in which the ions are moving with the carrier gas, the ions are deflected; the deflection distance is characteristic of the sizes of the ions and their interactions with the supporting gas atmosphere. Accordingly, ions of a particular mobility are separated from ions of all other mobilities present in an initial mixture.

In case one sort of ions has a specific mobility there are two ways to make use of a mobility analysis of a mixture of molecules. A. Finding in a mobility spectrum a peak that is characteristic of a molecule under consideration one has proof that this molecule was part of the initial mixture of molecules. B. Selecting ions that have the mentioned characteristic mobility one can guide these ions to an added analytical device, for instance a mass spectrometer.

Molecule ions of different mobilities can be separated from each other by registering the ion flight time in an accelerating field of given length [1], or by determining the deflection of that ion in an electric field that acts perpendicular to the motion of ions floating in a streaming gas [2].

Separation of ions is based on the differences of the mobilities K(E/N) of these ions varying with the magnitude of the electric field E and the density N of the gas in which the ions are moving. These variations differ for the different sorts of molecules a fact that is used in a "differential mobility spectrometer" [3], [4] in which a high frequency periodic asymmetric waveform of potentials causes, for a short time, a high-field, and for a longer time, a low-field, which forces the ions to oscillate normal to the direction of the carrier gas flow.

The differences in mobility between high and low-field conditions result in a net displacement of the ions, which progressively drift off-axis and eventually discharge on a set of electrodes which can also be used to confine the gas flow. This displacement can be compensated by the application of a dc-field, or alternatively, if a spectrum is required, by scanning a sawtooth-like compensation voltage so that only ions within a certain mobility range are transmitted and recorded consecutively on a Faraday plate.

[1] U.S. Pat. Nos. 3,639,757, 3,697,748, 3,812,355, 3,621,239

U.S. Pat. No. 5,047,723

U.S. Pat. No. 6,774,360; U.S. Pat. No. 6,621,077; U.S. Pat. No. 6,774,360

U.S. Pat. No. 6,495,823 B1, CCCP Patent 966583

Patent Application PCT/US2006/019747, filed May 22, 2006 (H. Wollnik)

The high-frequency fields in a "differential mobility spectrometer" are formed by applying high-voltage pulses to the electrodes of such a device. In the related art, these pulses are produced by transformer based electronic circuits, in which case the time integral over the positive pulses equals the time integral over the negative pulses, even though the voltages are not constant over the duration of the positive and negative pulses.

In the related art, one uses voltage pulses that have a strong sinusoidal half-wave over the short pulse and a sinus double-wave or triple-wave over the long pulse. As a consequence, in neither one of these pulses do the ions move in a constant field. Thus, the mobilities of the ions vary over the time of each pulse, which in turn compromises the finally achieved separation of ions of different molecules, which in turn comprises the desired resolving power, i.e., the ratio of the width of a peak in the mobility spectrum and the separation of the peak under consideration from other peaks.

Accordingly, it is desirable for the foregoing resolving power to be high, and there is thus a need for a means that improves this resolving power.

SUMMARY OF THE INVENTION

Aspects of the exemplary embodiments of the present invention include a differential mobility spectrometer having at least two electrodes to which electronically controlled fast varying potentials are supplied that create a high frequency multipole field whose biggest component is a dipole field to which a low frequency sawtooth-like substantially dipole field can be added as well as a constant DC-off-set substantially dipole field. The high-frequency waveform is formed by switching electronically controlled high voltages such that a repetitive pattern of at least one positive and/or at least one negative substantially rectangular pulse is formed in each high-frequency cycle. The heights and widths of these pulses are controlled independently with rise and fall times that are short as compared to the widths of the pulses.

BRIEF DESCRIPTION OF THE DRAWINGS

The above and/or other aspects of the present invention will become apparent and more readily appreciated from the following description of the exemplary embodiments, taken in conjunction with the accompanying drawings, in which.

DETAILED DESCRIPTION OF THE EXEMPLARY EMBODIMENTS

Figure 1:
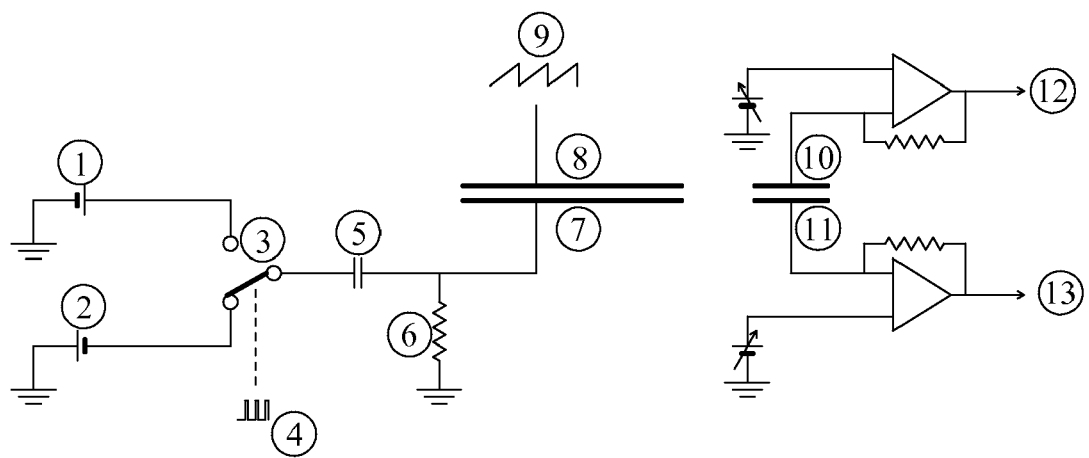
FIG. 1 is a schematic diagram of an exemplary embodiment of a digital-drive electronic circuit for a differential mobility spectrometer.

Reference will now be made in detail to exemplary embodiments of the present invention, examples of which are illustrated in the accompanying drawings, wherein like reference numerals refer to like elements throughout. The exemplary embodiments are described below so as to explain the present invention by referring to the figures.

In the exemplary embodiment, the pulsed voltages are not supplied from transformer based systems, but are instead supplied from switched voltages. Accordingly, the voltages and thus the fields, as well as the mobilities, are substantially constant over the duration of each of the produced high-frequency pulses.

In the circuits according to the exemplary embodiment, it is possible to control the amplitudes and durations of each pulse independently. For a given amplitude and durations of these voltage-pulses and field-pulses, the only ions that can reach the ion detectors directly are those ions having mobilities during the high-field pulse and during the low-field that have specific values. Ions that have different mobilities during these pulses will be deflected. These deflected ions can also be recorded one after the other if a slowly varying sawtooth-like voltage is added to the electrodes of the differential mobility spectrometer, and/or optionally, a DC offset voltage and thus also a DC off set field.

Figure 2:
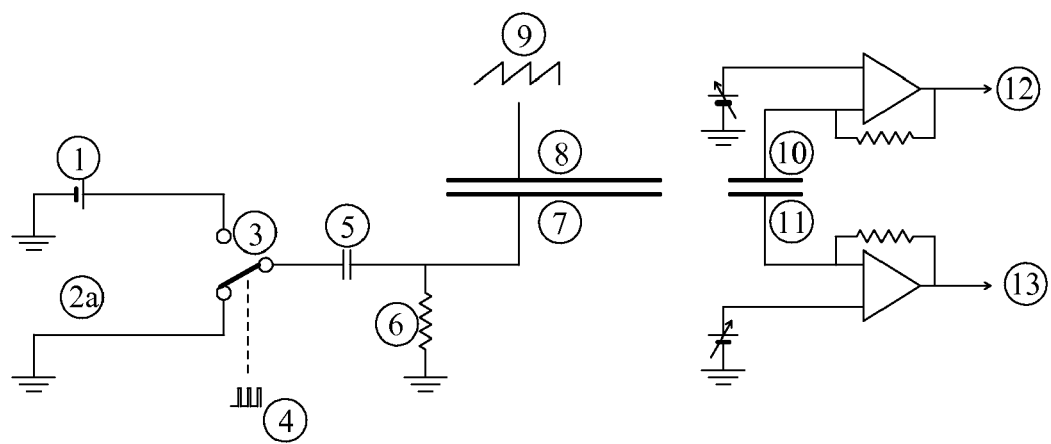
FIG. 2 is a variation of the exemplary embodiment of FIG. 1, where only one power supply is used.

Exemplary electronic circuit embodiments are shown in FIGS. 1 and 2.

FIG. 1 illustrates an exemplary circuit that uses one positive power supply and one negative power supply, which, for the duration of the high-frequency positive and negative pulses, supply corresponding voltages to one of the electrodes of the differential mobility spectrometer. More specifically, FIG. 1 illustrates a schematic diagram of an exemplary digital-drive electronic circuit for a differential mobility spectrometer.

According to the exemplary embodiment in FIG. 1, two power supplies 1, 2 are provided. The voltage of one of the power supplies 1 or 2 is supplied to one of the electrodes 7, 8 of the differential mobility spectrometer through a capacitor 5, to which the voltage is delivered through a fast switch 3 controlled by a digital signal 4. The capacitor 5 is coupled to a resistor 6 to form an RC circuit, which establishes a reference of the waveform to ground potential, and removes any dc-offset component.

To the second electrode 8 of the differential mobility spectrometer, a low frequency sawtooth voltage is 9 applied. Transmitted positive and negative ions are collected on detector plates 10 and 11, respectively. Amplified signals 12 and 13 are fed to a data acquisition system.

FIG. 2 illustrates an exemplary circuit according to the present invention. Reference characters that are the same as in FIG. 1 have the same structure, and their description is not repeated for the sake of brevity.

In contrast to FIG. 1, the exemplary embodiment of FIG. 2 uses only one power supply 1 that delivers a voltage as great as the sum of the absolute values of the voltages of the two power supplies of FIG. 2. The switch 3 connects either the power supply 1 or a ground 2a to the capacitor 5 and thus to one of the electrodes 7, 8 of the differential mobility spectrometer.

In the exemplary embodiments shown in FIG. 1 and FIG. 2, the low-frequency sawtooth-like voltage generator and the optional DC off set voltage are supplied to the other electrode of the differential mobility spectrometer.

The exemplary method of summing the high-frequency and low-frequency signals, i.e., applying all high-frequency signals to one of the electrodes of the differential mobility spectrometer and all low-frequency signals to the other electrode, can be modified without departing from the scope of the invention.

For example but not by way of limitation, all the different signals in an electric circuit can be summed. This sum of voltages can be applied to one of the electrodes of the differential mobility spectrometer, while the other electrode is kept at ground potential.

Figure 3:
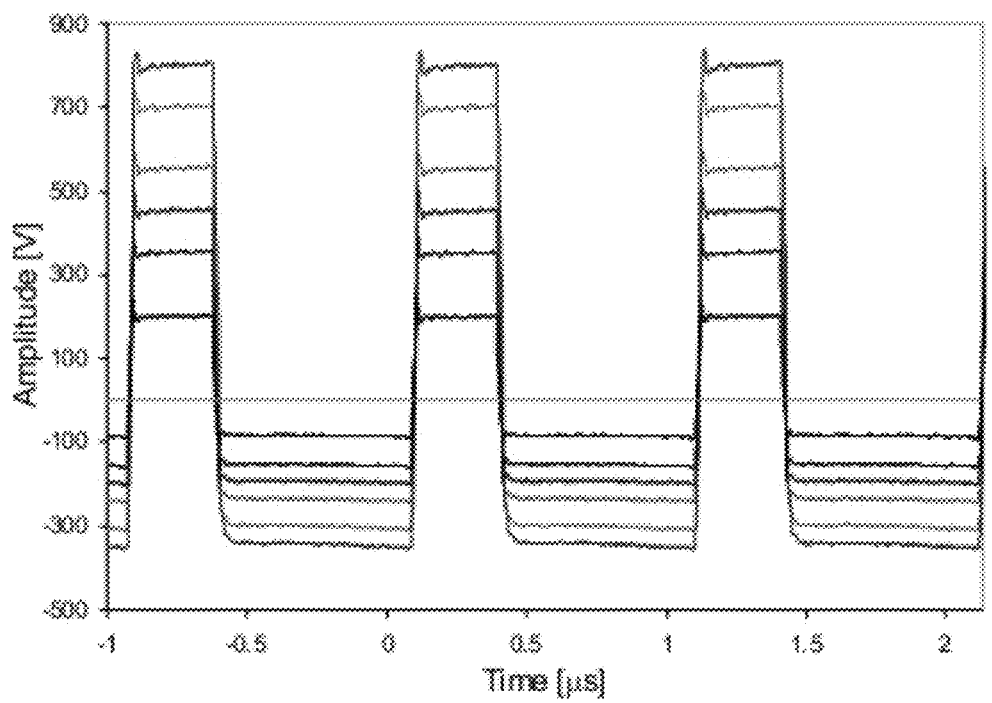
FIG. 3 is an oscillogram of a rectangular waveform showing high voltage positive and lower voltage negative pulses, according to the exemplary embodiment.

FIG. 3 illustrates the experimentally obtained high-frequency waveform demonstrating pulse rise times of <100 ns and optionally varied amplitudes of the positive and the negative pulses. More specifically, FIG. 3 is an oscillogram of a rectangular waveform showing high voltage positive and low voltage negative pulses, for which the rise and fall times are substantially small compared to the duration of the pulses. For example, the frequency is about 1 MHz, and the duty cycle of the positive pulse is about 30% of the period of the waveform.

Figure 4:
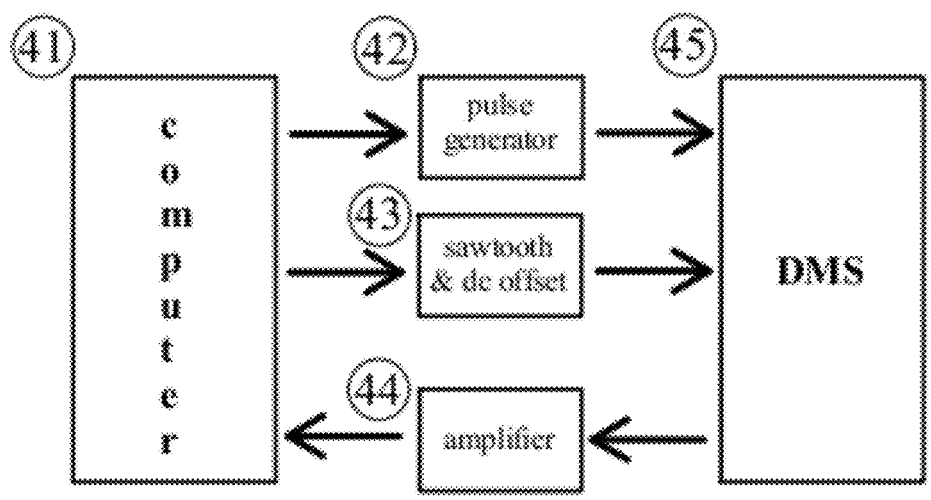
FIG. 4 shows a diagram of how the pulse generator as well as the sawtooth waveform and dc-offset are controlled by a computer according to the exemplary embodiment.

FIG. 4 illustrates the overall system, i.e., controls of the pulse widths and heights and the data analysis, being computer controlled. More specifically, the pulse generator 42 and the sawtooth waveform and dc-offset 43 are controlled by a computer 41. The amplified signal generated by the amplifier 44 is fed back to the computer 41. Accordingly, the differential mobility spectrometer (DMS) 45 is computer controlled.

Figure 5:
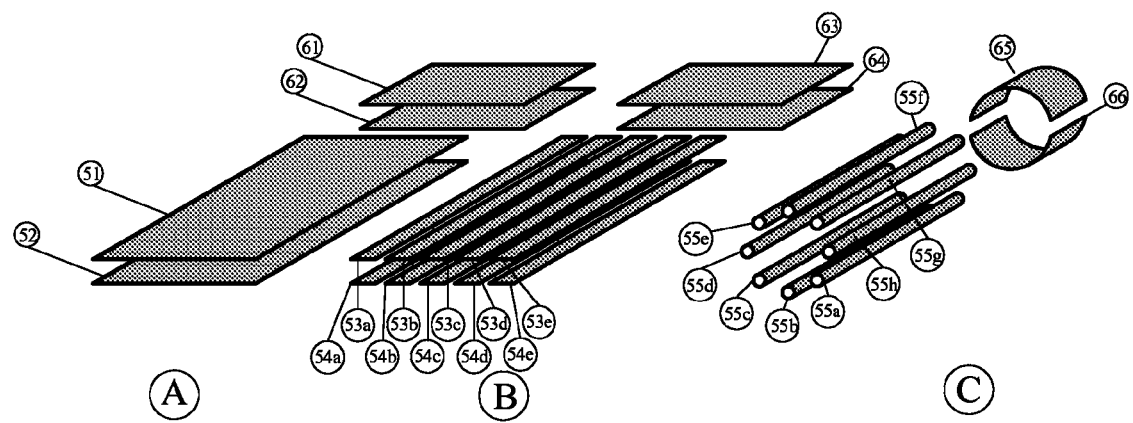
FIGS. 5A-5C show three electrode configurations of the differential mobility spectrometer according to the exemplary embodiment.

FIGS. 5A-5C illustrates the electrode arrangements of the differential mobility spectrometer shaped to different exemplary, non-limiting geometries. Configuration 1 in FIG. 5A includes two parallel plates 51, 52 and two separate co-planar detectors 61, 62, Configuration 2 in FIG. 5B includes a plate multipole 53, 54 and two separate co-planar detectors 63, 64. Configuration 3 in FIG. 5C includes a multipole 55a . . . 55h in which the electrodes are arranged on a cylinder. Also shown in configuration 3 is a set of detector-electrodes 65, 66 with possible but not limiting shapes.

As shown in the exemplary embodiment of FIG. 5A, co-planar electrodes 51, 52 comprise the electrodes of the differential mobility spectrometer that features a substantially dipolar field.

In another exemplary embodiment shown in FIG. 5B, two coplanar but segmented electrodes 53a . . . 53e, 54a . . . 54e are used which allow to shape the field of the differential mobility spectrometer to be a field as formed between two substantially concentric cylinder electrodes.

In the related art, two explicit concentric cylindrical electrodes form a radially inhomogeneous field in which the radius of the mid-equipotential surface comprises a cylinder surface whose radius is fixed. However, if a series of substantially parallel electrodes 53a ... e and 54a ... e used to which different high-frequency pulse voltages can be applied so that the final field equals that formed between two concentric cylinder electrodes with a substantially cylindrical mid-equipotential surface having a variable radius of curvature.

According to a third exemplary shape of the waveform illustrated in FIG. 5C, explicit electrodes 55a ... 55h are arranged along a circle as shown through arrangements substantially along an ellipse, square or rectangle are possible as well. In this exemplary embodiment, different high-frequency pulse voltages must be applied to the different electrodes, so as to form a dipole field or a field that can be obtained between two concentric cylinder electrodes 65, 66 with a substantially cylindrical mid-equipotential surface having a variable radius of curvature.

Figure 6:
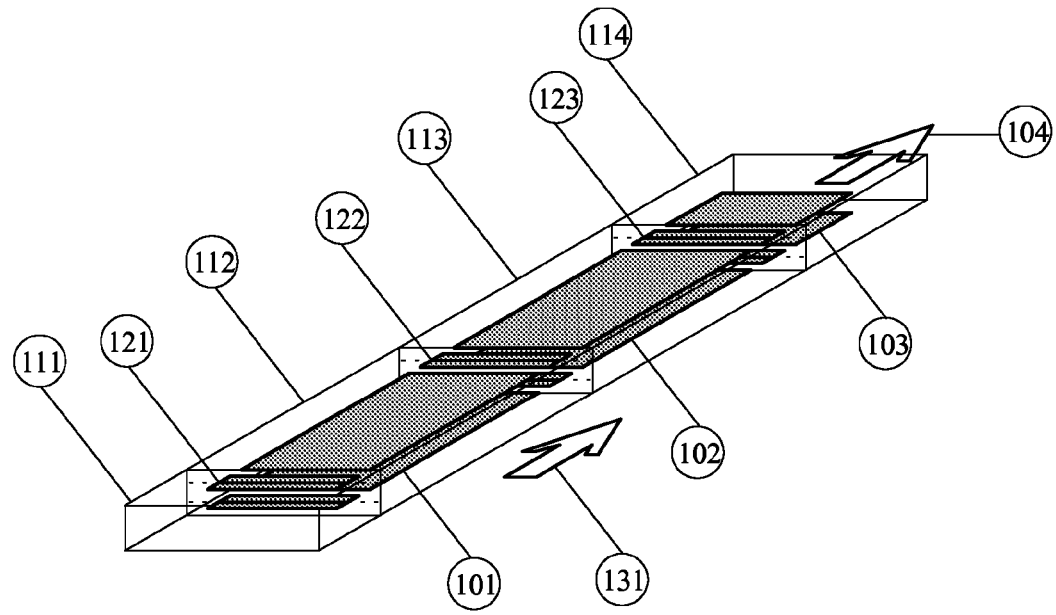
FIG. 6 shows an arrangement of two co-planar differential mobility spectrometers in series followed by a set of co-planar detector-electrodes and a possible connection to a mass spectrometer, according to an exemplary embodiment.

FIG. 6 shows an exemplary embodiment in which two or more differential mobility spectrometers are coupled in series. The different differential mobility spectrometers can be operated at different gas pressures as well as at different temperatures, and with different pulse amplitudes and pulse widths. This exemplary embodiment allows additional purifications over the use of a single differential mobility spectrometer.

More specifically, FIG. 6 shows an arrangement of two co-planar differential mobility spectrometers 101, 102 coupled in series, followed by a set of co-planar detector-electrodes 103 and an optional connection 104 to a mass spectrometer. This arrangement of differential mobility spectrometers is divided into four sections 111-114 that optionally define regions of different gas pressures and/or temperatures.

In addition, each differential mobility spectrometer 101, 102 can be operated at different frequencies, amplitudes and/or duty cycles. In the first section 111 ions are formed in an ion source and carried by gas flow 131 through the consecutive sections. In-between sections additional electrodes 121, 122, 123 are positioned so as to control the rf—fringing fields and substantially enhance ion transmission.

When an ion is moved through the differential mobility spectrometer by the gas flow, the ion should experience several thousand oscillations about the axis of the system. Thus, the frequency of the pulse train is substantially proportional to the velocity of the gas flow, and substantially inversely proportional to the length $L_{DMS}$ of the differential mobility spectrometer electrodes. For example but not by way of limitation, when $L_{DMS}$ is about 20 mm to about 40 mm, the pulse frequency is on the order of about several 100 kHz.

Figure 7:
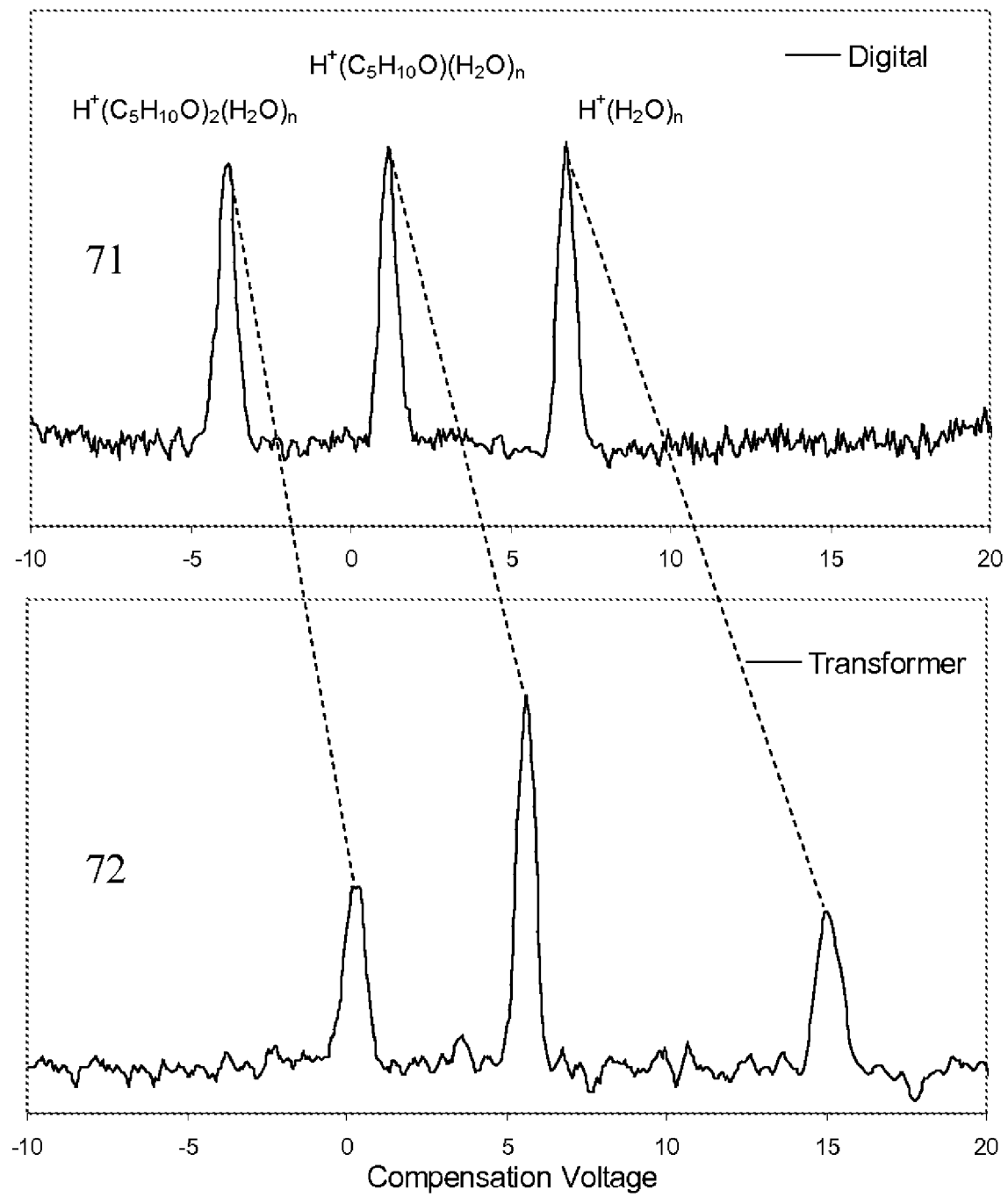
FIG. 7 shows two differential mobility spectra of hydrated protons as well as of monomer and dimmer ions of the molecules under consideration according to the exemplary embodiments.

The foregoing exemplary embodiments may improve the mobility resolving power over the related art system including a transformer based electronic circuit. Switch controlled voltages provide the highest fields for the full duration of the high-voltage and the low-voltage periods. Thus, also the maximum voltages in the high-voltage peaks may be substantially smaller than in transformer based systems, which only approximate square waves, as shown in FIG. 7. Alternatively maximal voltages in the high-voltage and low-voltage periods of the magnitude used in transformer based systems can provide substantially increased resolving powers.

FIG. 7 shows two differential mobility spectra of hydrated protons, $H^+(H_2O)_n$, protonated pentanone monomer, $H^+(C_5H_{10}O)(H_2O)_n$, and proton-bound pentanone dimer ions, $H^+(C_5H_{10}O)_2(H_2O)_n$, both obtained in air at ambient pressure. More specifically, in FIG. 7, the digital-differential mobility spectrum of pentanone is shown as obtained by a digital waveform at 1 MHz, $d_p=0.3$, SV=600V and obtained by a transformer-based waveform at 1 MHz, $d_p=0.3$, SV=1200V.

The first spectrum 71 shown at the top part of FIG. 7 was obtained when the differential mobility spectrometer was driven by a digital waveform generated by a high-voltage switched device. The second spectrum 72 shown at the bottom part of FIG. 7 was obtained when the differential mobility spectrometer was driven by the related art transformer based electronic circuitry.

In both of the foregoing spectra 71, 72, the frequencies were set at 1 MHz and the positive duty cycle was $d_p=30\%$. The amplitude of the high voltage pulse on the digital drive is 600 V, denoted as separation voltage (SV), and the peak of the transformer based electronics is 1200 V. The spectra illustrate the capability of the digital waveform 71 to separate ions at about half the voltage required when a related art transformer based waveform 72 is employed.

In the foregoing embodiments, the DMS units are coupled in series and may be operated at equal or different pressures and/or temperatures. The ions separated by differential mobility may also be entered into a mass spectrometer for an additional analysis. The ions are formed in atmospheric pressure ion sources which includes electrospray ion sources, laser desorption assisted electrospray ion sources, DESI (desorption electro-spray ionization) ion sources, MALDI (matris assisted laser desorption ionization) ion sources or coupled plasma ion sources. Alternatively, the ions may be formed at reduced pressure which includes photo-ionization sources, electron-impact-ion sources, chemical-ionization sources, surface-ionization sources, or MALDI ion sources.

According to the exemplary embodiment, it is also possible to divide the pulse train in different subcycles, and change the pulse height and/or the pulse duration from one cycle to the next. Furthermore, it is possible to supply more than one positive pulse and/or more than one negative pulse in each subcycle.

The exemplary embodiments may result in the resolving power in a differential mobility spectrometer powered by a "switched pulse supply" being substantially increased over a differential mobility spectrometer powered by a "transformer based supply". This increase is at least partially due to the fact that the widths of registered mobility peaks are slightly smaller.

Further, by varying the ratio of the time integrals over the positive and negative pulse, the mobility peaks of different molecules can be shifted so that their separation distance is increased, or that their overlap is reduced if the peaks are close to each other. Since the maximum amplitudes of the voltage pulses are substantially smaller than in a transformer based circuit, the Kilpatrick limit may be reduced so that the danger of a high-voltage breakthrough event may be reduced.

The exemplary embodiment is described above with reference to a controlling computer. It should be understood that control by the computer can be implemented by computer program instructions. These computer program instructions can be provided to a processor of a general purpose computer, special purpose computer, or other programmable data processing apparatus to produce a machine, such that the instructions, which are executed via the processor of the computer or other programmable data processing apparatus, create means for implementing the above functions of the differential mobility spectrometer.

These computer program instructions may also be stored in a computer usable or computer-readable memory that can direct a computer or other programmable data processing apparatus to function in a particular manner, such that the instructions stored in the computer usable or computer-readable memory produce an article of manufacture including instruction means that implement the functions.

The computer program instructions may also be loaded into a computer or other programmable data processing apparatus to cause operational steps to be performed in the computer or other programmable apparatus to produce a computer implemented process such that the instructions that are executed on the computer or other programmable apparatus provide steps for implementing the functions.

Although exemplary embodiments have been disclosed, it will be appreciated by those skilled in the art that changes may be made in these exemplary embodiments without departing from the principles and spirit of the invention, the scope of which is defined in the appended claims and their equivalents.

What is claimed is:

1. A digital-drive electronic circuit for a differential mobility spectrometer (DMS), comprising:

at least one power supply that supplies voltages to a first electrode and a second electrode of the DMS;

a resistor coupled to a capacitor so as to form an RC (resistor-capacitor) circuit that connects the at least one power supply and the first and second electrodes of the DMS;

a fast switch that connects the at least one power supply and the capacitor, said fast switch being controlled by a digital signal;

first and second detector plates that collect positive and negative ions transmitted from the DMS and provides corresponding signals to respective first and second amplifiers, so as to generate first and second amplified signals that are fed to a data acquisition system;

wherein a low frequency sawtooth voltage and/or a DC offset voltage is applied to the second electrode.

* * * * *